(12) United States Patent
Hirokawa

(10) Patent No.: US 10,695,369 B2
(45) Date of Patent: Jun. 30, 2020

(54) COGNITIVE FUNCTION-REMEDYING AGENT

(71) Applicant: Yoshihiro Hirokawa, Kyoto (JP)

(72) Inventor: Yoshihiro Hirokawa, Kyoto (JP)

(*) Notice: Subject to any disclaimer, the term of this patent is extended or adjusted under 35 U.S.C. 154(b) by 0 days.

(21) Appl. No.: 16/090,843

(22) PCT Filed: Apr. 13, 2017

(86) PCT No.: PCT/JP2017/015084
§ 371 (c)(1),
(2) Date: Oct. 3, 2018

(87) PCT Pub. No.: WO2017/179644
PCT Pub. Date: Oct. 19, 2017

(65) Prior Publication Data
US 2019/0117687 A1    Apr. 25, 2019

(30) Foreign Application Priority Data
Apr. 15, 2016  (JP) .................................. 2016-081881

(51) Int. Cl.
| | | |
|---|---|---|
| *A61K 33/30* | (2006.01) |
| *A61K 31/07* | (2006.01) |
| *A61K 31/197* | (2006.01) |
| *A61K 31/355* | (2006.01) |
| *A61K 31/4188* | (2006.01) |
| *A61K 31/4415* | (2006.01) |
| *A61K 31/51* | (2006.01) |
| *A61K 31/519* | (2006.01) |
| *A61K 31/525* | (2006.01) |
| *A61K 31/59* | (2006.01) |
| *A61K 31/714* | (2006.01) |
| *A61K 33/06* | (2006.01) |
| *A23L 33/16* | (2016.01) |
| *A61K 31/34* | (2006.01) |
| *A23L 33/15* | (2016.01) |
| *A23L 33/155* | (2016.01) |
| *A61P 25/00* | (2006.01) |
| *A61K 31/375* | (2006.01) |

(52) U.S. Cl.
CPC .............. *A61K 33/30* (2013.01); *A23L 33/15* (2016.08); *A23L 33/155* (2016.08); *A23L 33/16* (2016.08); *A61K 31/07* (2013.01); *A61K 31/197* (2013.01); *A61K 31/34* (2013.01); *A61K 31/355* (2013.01); *A61K 31/375* (2013.01); *A61K 31/4188* (2013.01); *A61K 31/4415* (2013.01); *A61K 31/51* (2013.01); *A61K 31/519* (2013.01); *A61K 31/525* (2013.01); *A61K 31/59* (2013.01); *A61K 31/714* (2013.01); *A61K 33/06* (2013.01); *A61P 25/00* (2018.01); *A23V 2002/00* (2013.01)

(58) Field of Classification Search
CPC ........ A23L 33/15; A23L 33/155; A23L 33/16; A23V 2002/00; A61K 31/07; A61K 31/197; A61K 31/34; A61K 31/355; A61K 31/375; A61K 31/4188; A61K 31/4415; A61K 31/51; A61K 31/519; A61K 31/525; A61K 31/59; A61K 31/714; A61K 33/06; A61K 33/30; A61K 2300/00; A61K 31/11; A61K 31/592; A61K 31/593; A61P 25/00; A61P 25/28
See application file for complete search history.

(56) References Cited

U.S. PATENT DOCUMENTS

| | | | |
|---|---|---|---|
| 2006/0121133 A1* | 6/2006 | Chomczynski | A61K 31/045 424/736 |
| 2009/0196862 A1* | 8/2009 | Davis | A61K 31/593 424/94.1 |
| 2013/0330428 A1* | 12/2013 | Geng | A61K 36/185 424/729 |
| 2014/0256808 A1* | 9/2014 | Henderson | A23L 2/52 514/546 |

FOREIGN PATENT DOCUMENTS

| | | |
|---|---|---|
| DE | 20/2014/102551 U1 | 4/2015 |
| JP | 2009/532496 A | 9/2009 |
| JP | 5300196 B2 | 9/2013 |
| JP | 2014/534225 A | 12/2014 |
| RU | 2009/138159 A | 10/2009 |
| WO | WO-2005/074956 A1 | 8/2005 |

(Continued)

OTHER PUBLICATIONS

Aisen et al "High Dose B Vitamin Supplementation and Cognitive Decline in Alzheimer's Disease: A Randomized Controlled Trial" The Journal of the American Medical Association vol. 300, pp. 1774-1783, 2008.

Arit et al "Effect of One-Year Vitamin C- and E-Supplementation on Cerebrospinal Fluid Oxidation Parameters and Clinical Course in Alzheimer's Disease" Neurochemical Research vol. 37, pp. 2706-2714, 2012.

Kang et al "Vitamin E, Vitamin C, Beta Carotene, and Cognitive Function Among Women With or at Risk of Cardiovascular Disease" Circulation vol. 119, pp. 2772-2780, 2009.

(Continued)

*Primary Examiner* — Mark V Stevens
(74) *Attorney, Agent, or Firm* — Cesari and McKenna, LLP

(57) ABSTRACT

Disclosed are a cognitive function improvement agent comprising vitamin A, vitamin B components ($B_1$, $B_2$, $B_6$, and $B_{12}$), vitamin C, vitamin D, vitamin E, zinc, magnesium, pantothenic acid, biotin, and folic acid as active ingredients, and a method for improving cognitive functions, comprising administering vitamin A, vitamin B components ($B_1$, $B_2$, $B_6$, and $B_{12}$), vitamin C, vitamin D, vitamin E, zinc, magnesium, pantothenic acid, biotin, and folic acid to a mammal.

8 Claims, No Drawings

(56) References Cited

FOREIGN PATENT DOCUMENTS

WO  WO-2007/115282 A2  10/2007
WO  WO-2013/066151 A1  5/2013

OTHER PUBLICATIONS

Petersen et al "Vitamin E and Donepezil for the Treatment of Mild Cognitive Impairment" The New England Journal of Medicine vol. 352, pp. 2379-2388, 2005.
Van Uffelen et al "Walking or Vitamin B for Cognition in Older Adults with Mild Cognitive Impairment? A Randomised Controlled Trial" The American Journal of Sports medicine vol. 42, pp. 344-351, 2008.
Supplementary European Search Report dated Jan. 17, 2020 for EP patent application No. 17 782 457.0.

* cited by examiner

COGNITIVE FUNCTION-REMEDYING AGENT

CROSS-REFERENCE TO RELATED APPLICATIONS

This application is the National Stage of International Application No. PCT/JP2017/015084, filed April 13, 2017, which claims the benefit of Japanese Application No. 2016-081881, filed April 15, 2016. The contents of both applications are hereby incorporated by reference in their entirety.

TECHNICAL FIELD

The present invention relates to a cognitive function improvement agent and a method for improving cognitive functions.

BACKGROUND ART

With the aging of the population, dementia patients have continued to increase, which has become a significant social issue in Japan. Mild cognitive impairment (MCI) is a stage before dementia, and the number of elderly people who have MCI is presumably quite large.

MCI is a symptom at the intermediate stage (gray area) between dementia and the healthy state of a person. MCI is a state in which one of the cognitive functions (memory, determination, reasoning, execution, etc.) has a problem, but daily activities can be performed without any difficulty. When left untreated, MCI continues to reduce cognitive functions, and about half of all MCI patients are considered to progress to the stage of dementia. Since there is so far basically no cure for dementia, it is highly important to take appropriate action at the MCI stage to prevent the progression of symptoms.

There are mainly four types of dementia: Alzheimer's dementia, Lewy body dementia, vascular dementia, and frontotemporal dementia.

Of these, Alzheimer's disease is the most common dementia and accounts for more than half of all cases of senile dementia. Alzheimer's disease is characterized by progressive dementia occurring from the presenile stage to the senile stage, and the number of patients in Japan nowadays is thought to be 3 million or more. Clinical symptoms of Alzheimer's disease include memory impairment, higher-brain dysfunction (e.g., apraxia, agnosia, aphasia, and constructional apraxia), etc. The deposition of amyloid β protein and tau protein in the brain causes neuron death, which is thought to be the cause of Alzheimer's disease.

Four anti-dementia medications (donepezil, memantine, galantamine, and rivastigmine) are currently used to treat dementia. It is generally thought that administration of one or two medications among the four medications can delay the progression of dementia.

In order for the brain to function smoothly, sufficient ATP (adenosine triphosphate) is required as an energy source, but most dementia patients have reduced ATP production. ATP production decreases every year after age 40, and ATP production at age 80 is said to be about 60, based on 100 at age 40. A reduction in ATP level accelerates the decline in cognitive functions (specifically, dementia is more likely to develop), but the four anti-dementia medications cannot increase the ATP level although they increase acetylcholine in the brain. Moreover, although a cerebral circulation metabolism improvement agent can be used to promote ATP production, it can be used only after organic dysfunction, such as cerebral infarction, under the current system.

Patent Literature 1 has reported that there is a possibility of using a Ginkgo biloba extract, combined with phosphatidylserine, as an active ingredient of a food or drug for improving dementia and Alzheimer's disease. On the other hand, some documents have reported that supplements containing vitamin B, vitamin C, vitamin E, β-carotene, folic acid, etc., either singly or in a combination of 2 or 3 or so, are not effective for improving cognitive functions (Non-patent literature 1 to 5).

CITATION LIST

Patent Literature

PTL 1: U.S. Pat. No. 5,300,196

Non-Patent Literature

NPL 1: Art S et al., Neurochem Res 37: 2706-2714, 2012
NPL 2: Petersen R C et al., N Engl J Med 352: 2379-2388, 2005
NPL 3: Kang J H et al., Circulation 119: 2772-2780, 2009
NPL 4: Aisen P S et al., JAMA 300: 1774-1783, 2008
NPL 5: van Uffelen J G et al., Br J Sports Med 42: 344-351, 2008

SUMMARY OF INVENTION

Technical Problem

An object of the present invention is to provide a cognitive function improvement agent having an effect of improving cognitive functions, and a method for improving cognitive functions.

Solution to Problem

As stated above, failure in increasing ATP production is believed to be the underlying cause of unsatisfactory results of current dementia treatment with anti-dementia medications. ATP is produced through seven-stage reactions of the TCA cycle, and vitamins play important roles as coenzymes in each reaction. Specifically, sufficient vitamin supplementation may promote ATP production.

The inventors conducted extensive research to achieve the above object. As a result, they found that the object can be achieved by a supplement comprising vitamin A, vitamin B components ($B_1$, $B_2$, $B_6$, and $B_{12}$), vitamin C, vitamin D, vitamin E, zinc, magnesium, pantothenic acid, biotin, and folic acid.

The present invention was accomplished as a result of further research based on these findings, and provides a cognitive function improvement agent etc., shown below.

Item 1

A cognitive function improvement agent comprising vitamin A, vitamin B components ($B_1$, $B_2$, $B_6$, and $B_{12}$), vitamin C, vitamin D, vitamin E, zinc, magnesium, pantothenic acid, biotin, and folic acid as active ingredients.

Item 2

The cognitive function improvement agent according to Item 1, wherein vitamin D is contained in an amount of 0.0008 mass % or more.

Item 3

The cognitive function improvement agent according to Item 1 or 2, wherein vitamin A is contained in an amount of 0.085 mass % or less.

Item 4

The cognitive function improvement agent according to any one of Items 1 to 3, wherein zinc is contained in an amount of 0.35 mass % or less.

Item 5

Use of vitamin A, vitamin B components ($B_1$, $B_2$, $B_6$, and $B_{12}$), vitamin C, vitamin D, vitamin E, zinc, magnesium, pantothenic acid, biotin, and folic acid for producing a cognitive function improvement agent (cognitive function improvement food for health uses).

Item 6

A method for improving cognitive functions, comprising administering vitamin A, vitamin B components ($B_1$, $B_2$, $B_6$, and $B_{12}$), vitamin C, vitamin D, vitamin E, zinc, magnesium, pantothenic acid, biotin, and folic acid to a mammal.

Item 7

A composition for improving cognitive functions comprising vitamin A, vitamin B components ($B_1$, $B_2$, $B_6$, and $B_{12}$). vitamin C, vitamin D, vitamin E, zinc, magnesium, pantothenic acid, biotin, and folic acid.

Advantageous Effects of Invention

The cognitive function improvement agent of the present invention has an effect of improving cognitive functions of MCI and dementia patients.

Although the single use of the cognitive function improvement agent of the present invention exhibits an effect, the combination use with an anti-dementia medication effectively delays the progression of dementia and improves cognitive functions. Further, the cognitive function improvement agent of the present invention can be expected to maintain the activities of daily living (ADLs) of MCI and dementia patients.

DESCRIPTION OF EMBODIMENTS

The present invention is explained in detail below.

In this specification, the term "comprise" encompasses the meanings of "consist essentially of" and "consist of."

The cognitive function improvement agent of the present invention comprises vitamin A, vitamin B components ($B_1$, $B_2$, $B_6$, and $B_{12}$), vitamin C, vitamin D, vitamin E, zinc, magnesium, pantothenic acid, biotin, and folic acid as active ingredients.

Examples of vitamin A used in the present invention include vitamin $A_1$ (retinol), retinal, retinoic acid, vitamin $A_2$ (3-dehydroretinol), 3-dehydroretinal, 3-dehydro retinoic acid, derivatives thereof, esters thereof, provitamin A, salts thereof, etc. Examples of esters include esters with various fatty acids (e.g., retinol acetate). Examples of provitamin A include α-carotene, β-carotene, γ-carotene, δ-carotene, lycopene, zeaxanthin, β-cryptoxanthin, echinenone, etc. Vitamin A can be used singly or in a combination of two or more. As vitamin A in the present invention, those isolated from natural products and those produced by chemical synthesis can both be used.

Examples of vitamin $B_1$ used in the present invention include thiamine, salts thereof, etc. As vitamin $B_1$ in the present invention, those isolated from natural products and those produced by chemical synthesis can both be used.

Examples of vitamin $B_2$ used in the present invention include riboflavin, salts thereof, etc. As vitamin $B_2$ in the present invention, those isolated from natural products and those produced by chemical synthesis can both be used.

Examples of vitamin $B_6$ used in the present invention include pyridoxine, pyridoxalisol, pyridoxamine, salts thereof, etc. Vitamin $B_6$ can be used singly or in a combination of two or more. As vitamin $B_6$ in the present invention, those isolated from natural products and those produced by chemical synthesis can both be used.

Examples of vitamin $B_{12}$ used in the present invention include cobalamin, hydroxocobalamin, adenosylcobalamin, methylcobalamin, cyanocobalamin, sulfite cobalamin, salts thereof, etc. Vitamin $B_{12}$ can be used singly or in a combination of two or more. As vitamin $B_{12}$ in the present invention, those isolated from natural products and those produced by chemical synthesis can both be used.

Examples of vitamin C used in the present invention include ascorbic acid, salts thereof, etc. As vitamin C in the present invention, those isolated from natural products and those produced by chemical synthesis can both be used.

Examples of vitamin D (calciferol) used in the present invention include vitamin $D_2$ to $D_7$, provitamin $D_2$ to $D_7$, salts thereof, etc. Preferable examples of vitamin D used in the present invention include vitamin $D_2$, vitamin $D_3$, provitamin $D_2$, and provitamin $D_3$. Vitamin D can be used singly or in a combination of two or more. As vitamin D in the present invention, those isolated from natural products and those produced by chemical synthesis can both be used.

Examples of vitamin E used in the present invention include α-tocopherol, β-tocopherol, γ-tocopherol, δ-tocopherol, α-tocotrienol, β-tocotrienol, γ-tocotrienol, δ-tocotrienol, salts thereof, etc. Vitamin E can be used singly or in a combination of two or more. As vitamin E in the present invention, those isolated from natural products and those produced by chemical synthesis can both be used.

Examples of magnesium used in the present invention include magnesium, salts thereof, etc. Examples of magnesium salts include magnesium oxide, magnesium chloride, magnesium carbonate, magnesium sulfate, etc. Magnesium can be used singly or in a combination of two or more. As magnesium in the present invention, those isolated from natural products and those produced by chemical synthesis can both be used.

Examples of zinc used in the present invention include zinc, salts thereof, etc. Examples of organic acid salts of zinc include zinc pyrophosphate, zinc citrate, zinc succinate, zinc gluconate, etc. Examples of inorganic acid salts of zinc include zinc chloride, zinc sulfate, etc. Zinc can be used singly or in a combination of two or more. As zinc in the present invention, those isolated from natural products and those produced by chemical synthesis can both be used. As zinc in the present invention, zinc-containing materials such as zinc yeasts and oysters can be used without any treatment, or crudely purified for use.

Examples of pantothenic acid used in the present invention include pantothenic acid, salts thereof, etc. As pantothenic acid in the present invention, those isolated from natural products and those produced by chemical synthesis can both be used.

Examples of biotin used in the present invention include biotin, salts thereof, etc. As biotin in the present invention, those isolated from natural products and those produced by chemical synthesis can both be used. As biotin in the present invention, biotin-containing materials, such as biotin-containing yeasts, can be used without any treatment, or crudely purified for use.

Examples of folic acid used in the present invention include folic acid, derivatives of folic acid, salts thereof, etc.

As folic acid in the present invention, those isolated from natural products and those produced by chemical synthesis can both be used.

The amounts of vitamin A, vitamin B components ($B_1$, $B_2$, $B_6$, and $B_{12}$), vitamin C, vitamin D, vitamin E, zinc, magnesium, pantothenic acid, biotin, and folic acid in the cognitive function inhibitor of the present invention are not limited. For example, the amount of each active ingredient can be determined to comply with the amount of intake for an adult per day explained below.

The amount of vitamin A in the cognitive function improvement agent of the present invention is not limited and is preferably 0.00001 mass % or more, more preferably 0.0001 mass % or more, and preferably 0.085 mass % or less, more preferably 0.0085 mass % or less.

The amount of vitamin D in the cognitive function improvement agent of the present invention is not limited and is preferably 0.0008 mass % or more, more preferably 0.0010 mass % or more, and preferably 0.0068 mass % or less, more preferably 0.0021 mass % or less.

The amount of zinc in the cognitive function improvement agent of the present invention is not limited and is preferably 0.0001 mass % or more, more preferably 0.001 mass % or more, and preferably 0.35 mass % or less, more preferably 0.28 mass % or less.

The cognitive function improvement agent of the present invention includes the meanings of drugs, quasi-drugs, and foods and beverages (for example, health food, nutritional compositions, dietary supplement food, functional food, dietary supplement food, supplements, food for health uses, food for specified health uses, food with nutrient function claims, and food with function claims). The cognitive function improvement agent of the present invention also includes the meaning of an additive that imparts cognitive function improvement effects.

In addition to the active ingredients mentioned above, the foods and beverages mentioned above can optionally include minerals, vitamins, flavonoids, quinones, polyphenols, amino acids, nucleic acids, essential fatty acids, enzymes, starches, edible fats and oils, sweeteners, acidulants, bitterants, seasonings, colorings, flavorings, preservatives, bleaches, production agents, refrigerants, thickeners, emulsifiers, stabilizers, preservatives, baking powders, surfactants, bonding agents, resolvents, wetting agents, excipients, lubricants, binders, disintegrators, antioxidants, pH adjusters, brightening agents, gum base, etc.

Examples of foods and beverages include those ingestible by mammals (including humans), such as milk products; fermented foods (yogurt, cheese, etc.); drinks (coffee, juice, cocoa, tea drink, isotonic drink, energy drink, and like soft drinks; milk beverages; lactic acid bacteria beverages; lactic-acid-bacteria-containing beverages; yogurt beverages; carbonated beverages; sake, liquor, fruit wine, and like alcohols; etc.); spreads (custard cream etc.); pastes (fruit pastes etc.); Western-style confectioneries (chocolates, doughnuts, pies, choux, gum, gummy candies, jelly, candies, cookies, cakes, pudding, biscuits, etc.); Japanese sweets (daifuku (soft round rice cake stuffed with sweet bean jam), mochi (rice cake), manju (steamed azuki bean jam-filled bun), kasutera (Castilla cakes), anmitsu (agar jelly served with red bean paste and brown sugar syrup), youkan (sweet jellied adzuki-bean paste), senbei (rice crackers), okaki (small rice crackers), candies, etc.); frozen desserts (ice cream, ice candies, sherbets, etc.); food (curry, beef bowl, porridge of rice and vegetables, miso soup, soup, meat sauce, pasta, pickles, jam, ham, sausage, bacon, etc.); and seasonings (dressing, furikake (dried food sprinkled over rice), flavor enhancers, soup base, miso, soy sauce, sauce, catsup, oyster sauce, etc.).

The unit dosage form used as a supplement etc. is not limited and can be suitably selected. Examples include tablets (e.g., uncoated tablets, sugar-coated tablets, film-coated tablets, chewable tablets, and troches), capsules, fine granules, granules, solutions, powders, syrup, pastes, drinks, etc.

There is no limitation on the methods for producing the foods and beverages mentioned above. The foods and beverages can be produced by using known methods.

The intake amount of the cognitive function improvement agent of the present invention can be suitably selected according to the body weight, age, gender, symptoms, and various other conditions of the person taking the agent. The intake amount of each active ingredient in the cognitive function improvement agent of the present invention per day per adult is not limited and is, for example, as shown below.

Vitamin A: preferably 50 to 3,000 µg, more preferably 50 to 300 µg.

Vitamin $B_1$: preferably 25 to 200 mg, more preferably 50 to 150 mg.

Vitamin $B_2$: preferably 10 to 100 mg, more preferably 20 to 60 mg.

Vitamin $B_6$: preferably 10 to 100 mg, more preferably 20 to 60 mg.

Vitamin $B_{12}$: preferably 100 to 1,500 µg, more preferably 450 to 1,000 µg.

Vitamin C: preferably 100 to 5,000 mg, more preferably 1,000 to 3,000 mg.

Vitamin D: preferably 5 to 250 µg, more preferably 10 to 75 µg.

Vitamin E: preferably 50 to 800 mg, more preferably 67 to 400 mg.

Zinc: preferably 2 to 12 mg, more preferably 3 to 10 mg.

Magnesium: preferably 5 to 100 mg, more preferably 10 to 80 mg.

Pantothenic acid: preferably 50 to 400 mg, more preferably 120 to 300 mg.

Biotin: preferably 50 to 500 µg, more preferably 150 to 450 µg.

Folic acid: preferably 100 to 1,500 µg, more preferably 450 to 1,200 µg.

When the cognitive function improvement agent of the present invention is prepared as a quasi-drug or drug, the active ingredients can be prepared together with a non-toxic carrier, diluent, or excipient that is acceptable in pharmaceuticals, in the form of a tablet (including uncoated tablet, sugar-coated tablet, effervescent tablet, film-coated tablet, chewable tablet, troche, etc.), capsule, pill, dust (powder), fine granule, granule, solution, suspension, emulsion, syrup, paste, or injection (including a solution obtained by adding an injection to distilled water or a parenteral infusion such as an amino acid parenteral infusion or an electrolyte parenteral infusion at the time of use), thus preparing a pharmaceutical preparation.

Methods for administration of quasi-drugs or drugs are not limited. The quasi-drugs or drugs may be administered intra-arterially, intravenously, intra-orally, rectally, enterally, transdermally, orally, or in a like manner.

The administration amount of the quasi-drug or drug can be suitably determined according to the body weight, age, gender, symptoms, and various other conditions of the patient. The administration amounts of the active ingredients in the cognitive function improvement agent of the present invention per adult are not limited. For example, those mentioned above can be used.

By the combination use of 10 components, i.e., vitamin A, vitamin B components ($B_1$, $B_2$, $B_6$, and $B_{12}$), vitamin C, vitamin D, vitamin E, zinc, magnesium, pantothenic acid, biotin, and folic acid, the cognitive function improvement agent of the present invention exhibits an effect of improving cognitive functions (particularly, cognitive functions of pre-MCI, MCI, and dementia patients). Although this is not intended as being bound by any theory, it is believed that such an effect is obtained because supplementation of these 10 active ingredients promotes ATP production, which improves environment in the brain.

Thus, the cognitive function improvement agent of the present invention is used for the purpose of improving cognitive functions. "Cognitive functions" herein means functions impaired by dementia. The "cognitive functions" include memory, attentiveness, language function, function for performing a sequence of acquired actions, function for understanding a surrounding situation through the five senses, executive function, orientation, etc. "Dementia" is a state in which normally developed intelligence is irreversibly decreased by acquired organic brain damage. The term "improve" herein encompasses prevention of aggravation of symptoms, specifically, maintenance of symptoms.

Examples of the targets of the cognitive function improvement agent of the present invention include dementia (in particular, Alzheimer's disease) patients, MCI patients, pre-MCI patients, etc. For the purpose of maintaining cognitive functions, elderly people who have no problem with cognitive functions are also a target. The cognitive function improvement agent of the present invention is applied to mammals, including humans.

Although use of the cognitive function improvement agent of the present invention alone exhibits an effect, its use in combination with anti-dementia medications (donepezil, memantine, galantamine, rivastigmine, etc.) effectively delays the progression of dementia and improves cognitive functions. Further, the cognitive function improvement agent of the present invention can be expected to maintain the ADLs (activities of daily living) of MCI and dementia patients.

EXAMPLES

Example 1

The following Examples describe the present invention in further detail, but the invention is not limited to these examples.

Test Example

The cognitive function improvement agent of the present invention was examined in 10 cases. Of 10 test examples, 7 cases were pre-MCI patients with awareness of memory loss and easy fatigability. Three cases (Nos. 2, 3, and 10) were patients with awareness of memory loss and easy fatigability who were diagnosed as having pre-MCI, MCI, or dementia according to the Mini Mental State Examination (MMSE)[*1] and image diagnosis. After obtaining consent to a large amount of vitamin administration, predetermined amounts of vitamins were administered to these 10 cases, followed by monitoring over time. Specifically, capsules having the formulation shown in Table 1 below were administered to the subjects.

[*1] The Mini Mental State Examination (MMSE) is a 11-item questionnaire that is used worldwide as a screening test for dementia. The maximum score is 30 points.

TABLE 1

| Amounts of components in 9 capsules | |
|---|---|
| Vitamin A | 100 μg |
| Vitamin D | 50.0 μg |
| Vitamin E | 134.0 mg |
| Vitamin $B_1$ | 100.0 mg |
| Vitamin $B_2$ | 40.0 mg |
| Pantothenic acid | 240.0 mg |
| Vitamin $B_6$ | 40.0 mg |
| Biotin | 300 μg |
| Folic acid | 900 μg |
| Vitamin $B_{12}$ | 900.0 μg |
| Vitamin C | 2,000 mg |
| Magnesium | 60 mg |
| Zinc | 6.0 mg |

In the Test Example, the subjects were diagnosed or interviewed by a doctor before and after administration of capsules for a specific period.

Table 2 shows the results.

TABLE 2

| Case No. | Age | Gender | Drug treatment | Symptoms before administration | Dose/day | Period | Symptoms after administration | Improvement effect |
|---|---|---|---|---|---|---|---|---|
| 1 | 41 | Male | None | Aware of memory loss. Chronic fatigue from long-term, excessive stress and work. | 6 to 9 tablets | 2 months | Aware of alleviated memory loss. Felt mentally and physically improved. | Improved cognitive function Mental and physical improvement |
| 2 | 69 | Male | None | Felt mental fog and dizziness. Unaware of memory loss. | 6 to 9 tablets | 2 months | Felt mental clarity and clear vision (realized his vision had been foggy). | Improved cerebral blood flow Improved vision |
| 3 | 69 | Female | Memary, 5 mg | Aware of memory loss. Chronic fatigue from long-term, excessive work. | 6 to 9 tablets | 2 months | Still aware of memory loss, but felt no fatigue. | Mental and physical improvement |
| 4 | 81 | Female | None | Aware of memory loss. | 6 to 9 tablets | 2 months | Felt alleviated memory loss and no fatigue. | Improved cognitive function |

TABLE 2-continued

| Case No. | Age | Gender | Drug treatment | Symptoms before administration | Dose/day | Period | Symptoms after administration | Improvement effect |
|---|---|---|---|---|---|---|---|---|
| 5 | 54 | Female | None | Aware of memory loss. University lecturer/pharmacist. Chronic, long-term fatigue. | 6 to 9 tablets | 2 months | Aware of alleviated memory loss, and felt mentally and physically improved. | Mental and physical improvement Improved cognitive function Mental and physical improvement |
| 6 | 61 | Male | Memary, 5 mg | Aware of memory loss. Chronic fatigue from long-term, excessive stress and work. | 6 to 9 tablets | 2 months | Aware of alleviated memory loss, and felt mentally and physically improved. | Improved cognitive function Mental and physical improvement |
| 7 | 47 | Female | None | Aware of memory loss. | 6 to 9 tablets | 2 months | Aware of alleviated memory loss, and realized the administration effect the more severe the fatigue became. (Woke up feeling good in the morning.) | Improved cognitive function Mental and physical improvement |
| 8 | 45 | Male | None | Not aware of memory loss, but willing to take drugs for prevention. Tour bus driver. Chronic fatigue from excessive stress and work. | 6 to 9 tablets | 2 months | Administration of drugs apparently effective because felt poor without drugs. | Mental and physical improvement |
| 9 | 41 | Male | None | Not aware of memory loss, but willing to take drugs for prevention. As a dentist, has always strained in stressful use of his eyes. Chronic state of fatigue. | 6 to 9 tablets | 2 months | No longer tired easily, and felt alleviated eye fatigue. | Physical improvement Improved vision (due to Improved blood flow) |
| 10 | 73 | Male | Aricept 3 mg | Aware of memory loss. Lack of confidence. | 6 to 9 tablets | 2 months | Felt no longer tired easily. Possibility of memory loss, but sense of confidence. | Improved cognitive function Mental and physical improvement |

The 3 cases that were diagnosed as having pre-MCI, MCI, or dementia in the MMSE and image inspection were the cases in which Aricept, Reminyl, or Memary should have been used in an amount of about 8 to 10 mg, about 16 to 24 mg, and about 15 to 20 mg, respectively. However, the amounts of the drugs currently used were sufficient because of the use of the cognitive function improvement agent of the present invention. Further, in most of the cases, cognitive functions, as well as expressiveness, body agility, fatigue, motivation, etc., were improved, indicating that cerebral blood flow was significantly improved.

Although the other subjects, i.e., the 7 normal subjects, did not show significant improvement when taking other vitamins, they showed significant cognitive function improvement, recovery from fatigue, and recovery from eye fatigue when taking the agent of the present invention.

The invention claimed is:

1. A cognitive function improvement agent consisting essentially of vitamin A, vitamin $B_t$, vitamin $B_2$, vitamin $B_6$, vitamin $B_{12}$, vitamin C, vitamin D, vitamin E, zinc, magnesium, pantothenic acid, biotin, and folic acid as active ingredients in a form selected from a group consisting of a tablet, capsule, fine granule, granule, solution, powder, syrup, paste, and drink, wherein vitamin D is contained in an amount of 0.0008 mass % to 0.0068 mass % and vitamin A is contained in an amount of 0.00001 mass % to 0.085 mass %.

2. The cognitive function improvement agent according to claim 1, wherein zinc is contained in an amount of 0.0001 mass % to 0.35 mass %.

3. A method for improving cognitive functions, comprising administering a composition consisting essentially of vitamin A, vitamin $B_t$, vitamin $B_2$, vitamin $B_6$, vitamin $B_{12}$, vitamin C, vitamin D, vitamin E, zinc, magnesium, pantothenic acid, biotin, and folic acid to a mammal identified to be in need thereof, wherein vitamin D is contained in an amount of 0.0008 mass % to 0.0068 mass % and vitamin A is contained in an amount of 0.00001 mass % to 0.085 mass %.

4. The method according to claim 3, wherein zinc is contained in an amount of 0.0001 mass % to 0.35 mass %.

5. A cognitive function improvement agent consisting of vitamin A, vitamin $B_1$, vitamin $B_2$, vitamin $B_6$, vitamin $B_{12}$, vitamin C, vitamin D, vitamin E, zinc, magnesium, pantothenic acid, biotin, and folic acid as active ingredients and at least one pharmaceutically acceptable excipient in a form selected from a group consisting of a tablet, capsule, fine granule, granule, solution, powder, syrup, paste, and drink, wherein vitamin D is contained in an amount of 0.0008 mass % to 0.0068 mass % and vitamin A is contained in an amount of 0.00001 mass % to 0.085 mass %.

6. The cognitive function improvement agent according to claim 5, wherein zinc is contained in an amount of 0.0001 mass % to 0.35 mass %.

7. A method for improving cognitive functions, comprising administering a composition consisting of vitamin A, vitamin $B_1$, vitamin $B_2$, vitamin $B_6$, vitamin $B_{12}$, vitamin C, vitamin D, vitamin E, zinc, magnesium, pantothenic acid, biotin, folic acid, and at least one pharmaceutically acceptable excipient to a mammal identified to be in need thereof, wherein vitamin D is contained in an amount of 0.0008 mass % to 0.0068 mass % and vitamin A is contained in an amount of 0.00001 mass % to 0.085 mass %.

8. The method according to claim 7, wherein zinc is contained in an amount of 0.0001 mass % to 0.35 mass %.

* * * * *